US011000325B2

(12) United States Patent
Sommers et al.

(10) Patent No.: US 11,000,325 B2
(45) Date of Patent: May 11, 2021

(54) BONE FASTENER WITH PARTIALLY OVERLAPPING THREADS AND A VARYING LEAD

(71) Applicant: Acumed LLC, Hillsboro, OR (US)

(72) Inventors: Mark B. Sommers, Beaverton, OR (US); Terrence Chadwick Smith, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 122 days.

(21) Appl. No.: 15/907,187

(22) Filed: Feb. 27, 2018

(65) Prior Publication Data

US 2019/0262047 A1   Aug. 29, 2019

(51) Int. Cl.

| | | |
|---|---|---|
| *A61B 17/04* | (2006.01) | |
| *A61B 17/86* | (2006.01) | |
| *A61F 2/08* | (2006.01) | |
| *A61B 17/88* | (2006.01) | |
| A61B 17/56 | (2006.01) | |
| A61B 17/68 | (2006.01) | |

(52) U.S. Cl.
CPC ........ *A61B 17/863* (2013.01); *A61B 17/8635* (2013.01); *A61B 17/8645* (2013.01); *A61B 17/8875* (2013.01); *A61B 17/864* (2013.01); *A61B 2017/564* (2013.01); *A61B 2017/681* (2013.01)

(58) Field of Classification Search
CPC combination set(s) only.
See application file for complete search history.

(56) References Cited

U.S. PATENT DOCUMENTS

| | | |
|---|---|---|
| 4,712,541 A | 12/1987 | Harder et al. |
| 4,753,460 A | 6/1988 | Tung |
| 5,562,672 A | 10/1996 | Huebner et al. |
| 5,827,285 A | 10/1998 | Bramlet |

(Continued)

FOREIGN PATENT DOCUMENTS

| | | | |
|---|---|---|---|
| AU | 2015221418 A1 | 8/2016 | |
| EP | 1265542 A1 | 12/2002 | |

(Continued)

OTHER PUBLICATIONS

Acumed LLC "Acutrak 2 Headless Compression Screw System" accessed Sep. 7, 2017, 6 pgs.

(Continued)

*Primary Examiner* — Sameh R Boles
(74) *Attorney, Agent, or Firm* — K&L Gates LLP (57) ABSTRACT

A fastener for fixing bone and a method of fixing bone with the fastener. The fastener may be headless and may be configured to compress bone when driven into at least one bone and across a discontinuity formed by the bone. In an exemplary embodiment, the fastener includes a forward portion, a rear portion, a first thread having a plurality of revolutions in each of the forward and rear portions, and a second thread having a plurality of revolutions in the rear portion and none in the forward portion. The first thread may have a greater average lead in the forward portion than the rear portion. Revolutions of the first thread and the second thread may alternate with one another in the rear portion such that the rear portion is at least double-threaded.

20 Claims, 4 Drawing Sheets

(56) References Cited

U.S. PATENT DOCUMENTS

| | | | |
|---|---|---|---|
| 6,030,162 A * | 2/2000 | Huebner | A61B 17/1682 411/263 |
| 6,224,373 B1 | 5/2001 | Lee et al. | |
| 6,299,615 B1 | 10/2001 | Huebner | |
| 6,916,321 B2 | 7/2005 | TenHuisen et al. | |
| 6,984,235 B2 | 1/2006 | Huebner | |
| 7,677,891 B2 | 3/2010 | Niznick | |
| 8,070,786 B2 | 12/2011 | Huebner et al. | |
| 8,636,785 B2 | 1/2014 | Hes et al. | |
| 8,657,602 B2 | 2/2014 | Han et al. | |
| 9,131,946 B2 | 9/2015 | Larche et al. | |
| 9,232,964 B2 | 1/2016 | Freudiger et al. | |
| 9,387,023 B2 | 7/2016 | Sonntag et al. | |
| 9,681,930 B2 | 6/2017 | Thome et al. | |
| 2004/0006346 A1 | 1/2004 | Holmen et al. | |
| 2007/0233122 A1 * | 10/2007 | Denis | A61B 17/7037 606/247 |
| 2007/0233124 A1 | 10/2007 | Corrao et al. | |
| 2008/0188899 A1 | 8/2008 | Bottlang et al. | |
| 2011/0070558 A1 | 3/2011 | Park et al. | |
| 2013/0253594 A1 | 9/2013 | Zucherman et al. | |
| 2014/0199658 A1 | 7/2014 | Cottrell | |
| 2014/0336709 A1 | 11/2014 | Avidano et al. | |
| 2015/0201984 A1 | 7/2015 | Orbay et al. | |
| 2017/0196612 A1 | 7/2017 | Castaneda et al. | |

FOREIGN PATENT DOCUMENTS

| | | | |
|---|---|---|---|
| WO | 2012171011 A1 | 12/2012 | |
| WO | 2017085376 A1 | 5/2017 | |
| WO | 2017136801 A1 | 8/2017 | |

OTHER PUBLICATIONS

Copenheaver, Blain R., Authorized Officer, ISA/US Commissioner for Patents, "International Search Report" in connection with related International Application No. PCT/US2019/019726, dated May 8, 2019, 2 pgs.

Copenheaver, Blain R., Authorized Officer, ISA/US Commissioner for Patents, "Written Opinion of the International Searching Authority" in connection with related International Application No. PCT/US2019/019726, dated May 8, 2019, 7 pgs.

GP Implant LTD, "Spiral Shape Implant, 2.42 Internal Hex Implant", date accessed Jan. 15, 2018, 6 pgs.

Neodent, "CM Implant Line", accessed Sep. 7, 2017, 3 pgs.

National Trading Company, "NTC—Implant & Bone Management, SM Implant", accessed Sep. 7, 2017, 17 pgs.

Periobasics.Com, "Dental implant components and Current concepts of implant design", accessed Jul. 20, 2019, 14 pgs.

Ziacom Medical, "conical dental implant / titanium / external hexagon, ZM4(R)MT Ziacom Medical", accessed Jul. 20, 2019, 5 pgs.

Ziacom Medical, "External hexagonal connection implant—Connection ZM4MT", accessed Jul. 20, 2019, 3 pgs.

Zimmer Biomet, "MAX VPC Screw System", date accessed Sep. 7, 2017, 2 pgs.

* cited by examiner

BONE FASTENER WITH PARTIALLY OVERLAPPING THREADS AND A VARYING LEAD

The human skeleton is composed of 206 individual bones that perform a variety of important functions, including support, movement, protection, storage of minerals, and formation of blood cells. To ensure that the skeleton retains its ability to perform its important functions, and to reduce pain and disfigurement, fractured bones should be repaired promptly and properly. Typically, a fractured bone is treated using a fixation device, which stabilizes the fractured bone and keeps it aligned during healing.

A bone screw may be utilized as a fixation device by placing the screw across a fracture to attach fragments of a bone to one another. To encourage healing, the screw should apply compression that urges the fragments against one another at the fracture site. For example, the screw may be structured as a lag screw that is threaded only distally and has a proximal head. The lag screw draws proximal and distal bone fragments together as the head of the screw is tightened against the proximal fragment. However, the lag screw can lose compression readily since it is in threaded engagement only with the distal bone fragment.

A headless compression screw is available for fixing bone. The entire length of the screw can be driven into bone because the diameter of the screw's shaft increases only gradually toward the proximal end of the screw. The screw has a single external thread that traverses both the proximal and distal sections of the screw's shaft. The thread thus is configured to span the fracture and attach the screw directly to fragments on both sides of the fracture. In contrast to a standard bone screw, the thread has a varying pitch that decreases gradually toward the proximal end of the screw. Accordingly, the screw applies compression to the bone when it is installed. Although this type of screw is a very effective implant for bone fixation, the screw still can be improved.

SUMMARY

The present disclosure provides a fastener for fixing bone and a method of fixing bone with the fastener. The fastener may be headless, and may be configured to compress bone when driven into at least one bone and across a discontinuity formed by the bone. In an exemplary embodiment, the fastener includes a forward portion, a rear portion, a first thread having a plurality of revolutions in each of the forward and rear portions, and a second thread having a plurality of revolutions in the rear portion and none in the forward portion. The first thread may have a greater average lead in the forward portion than the rear portion. Revolutions of the first thread and the second thread may alternate with one another in the rear portion such that the rear portion is at least double-threaded.

DETAILED DESCRIPTION

The present disclosure provides a fastener for fixing bone and a method of fixing bone with the fastener. The fastener may be headless, and may be configured to compress bone when driven into at least one bone and across a discontinuity formed by the bone. In an exemplary embodiment, the fastener includes a forward portion, a rear portion, a first thread having a plurality of revolutions in each of the forward and rear portions, and a second thread having a plurality of revolutions in the rear portion and none in the forward portion. The first thread may have a greater average lead in the forward portion than the rear portion. Revolutions of the first thread and the second thread may alternate with one another in the rear portion such that threads are partially overlapping and the rear portion is at least double-threaded.

A headless compression screw for bone conventionally has a single thread. The use of a single thread makes it difficult to structure a forward section of the thread for optimal purchase in distal trabecular bone, and a rear section of the same thread for optimal purchase in proximal cortical bone. More particularly, a deep thread having a large pitch is better for use in trabecular bone, while a shallow thread with a small pitch is better for use in cortical bone. However, the difference in pitch necessary to optimize these different thread regions within a single thread would create a pitch differential that is too large, which would cause the screw to strip bone and lose compression when installed. Accordingly, the single thread is generally structured as a compromise between the need for a coarse thread in the forward section and a fine thread in the rear section, which can produce a thread having a pitch that is too small in the forward section and/or too large in the rear section. If the forward section of the thread has an undersized pitch, the forward section taps proximal bone excessively when passing through, due to the small and varying pitch of the thread. As a result, when the rear section of the thread enters proximal bone, the rear section meets chewed-up bone of poor integrity. Moreover, the forward section with an undersized pitch can disrupt the trabecular structure of distal bone, making threaded engagement less stable distally, too. Alternatively, if the forward section of the thread is optimized for trabecular bone, its rear section has an insufficient axial density of thread revolutions for optimal purchase in cortical bone.

The fasteners of the present disclosure can improve purchase in proximal bone and/or distal bone over a single-threaded compression screw, to achieve more compression. The forward portion of the fastener may have a thread covering a smaller fraction of the outside of the forward shaft, relative to the single-threaded screw, due to a larger lead of the first thread and an optional buttress threadform. The resulting lower linear density of thread revolutions in the forward portion may disturb less bone as the fastener is advanced, which increases purchase for forward and rear portions of the fastener. The rear portion, due to being multi-threaded (at least double-threaded), may have a smaller pitch (and a corresponding higher linear density of thread revolutions) than the single-threaded screw, for improved purchase in cortical bone. In some embodiments, the rear portion may have a constant lead (and pitch), which decreases stripping of bone and therefore also increases purchase. The forward portion of the fastener may have greater purchase strength than the rear portion, such that upon advancement of the fastener, the rear portion is pulled into bone while maintaining compression across the fracture. Furthermore, the fastener may be driven into bone more quickly because the lead of the first thread can be significantly greater than (e.g., up to about twice) the lead of the single-threaded screw in any portion(s) thereof.

The fastener may have any combination of the following features. The fastener may be cannulated. The outside diameter of the shaft in the forward portion of the fastener may be constant, while the outside diameter of the shaft may increase smoothly and gradually in the rear portion toward the proximal end of the fastener. The major diameter of the first thread (and the fastener) may be at a minimum in a waist portion of the fastener. The first thread may have a buttress threadform (a sloped distal flank and a perpendicular proximal flank) in the forward portion of the fastener, and the first and second threads each may have a unified threadform (a V-shape with symmetric distal and proximal flanks) in the rear portion.

Further aspects of the present disclosure are described in the following sections: (I) headless compression fasteners for bone, (II) composition and manufacture, (III) methods of fixing bone, and (IV) examples.

I. HEADLESS COMPRESSION FASTENERS FOR BONE

This section describes exemplary headless fasteners (interchangeably called screws) for fixing and compressing bone, with each fastener having a longer thread of varying lead and a shorter thread partially overlapping the longer thread longitudinally in a proximal portion of the fastener. Selected features of the fasteners described in this section are illustrated by an exemplary fastener 50; see FIG. 1-5.

Figure 1:
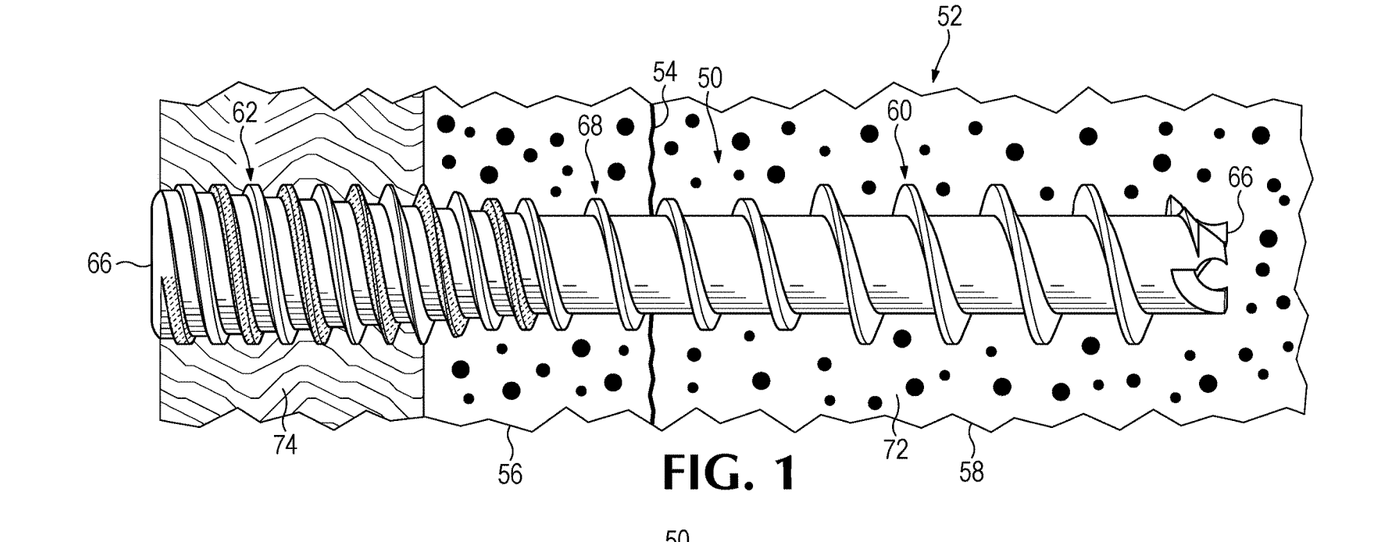
FIG. 1 is a side view of an exemplary headless fastener for fixing and compressing a fractured bone (depicted in cross-section), where the fastener has a first thread of variable lead traversing substantially the entire length of the fastener and a second thread partially overlapping the first thread and restricted to a proximal portion of the fastener, to create a single-threaded forward portion and a double-threaded rear portion of the fastener, in accordance with aspects of the present disclosure.

FIG. 1 shows an exemplary headless compression fastener 50 installed in, fixing, and compressing at least one bone 52, and FIGS. 2-5 show fastener 50 in isolation. The at least one bone may form a discontinuity 54 separating the bone into discrete bone pieces 56, 58, and the fastener may be partially located in each piece and may span the discontinuity (see FIG. 1). The discontinuity may be formed by a single bone, and bone pieces 56, 58 may be fragments of the single bone. Exemplary single-bone discontinuities that may be spanned by the fastener include a fracture, a cut, and a nonunion, among others. Alternatively, the discontinuity may be formed as a junction (e.g., a joint) between a pair of different bones. In this case, installation of the fastener may facilitate fusion of the bones with one another at the junction.

Figure 2:
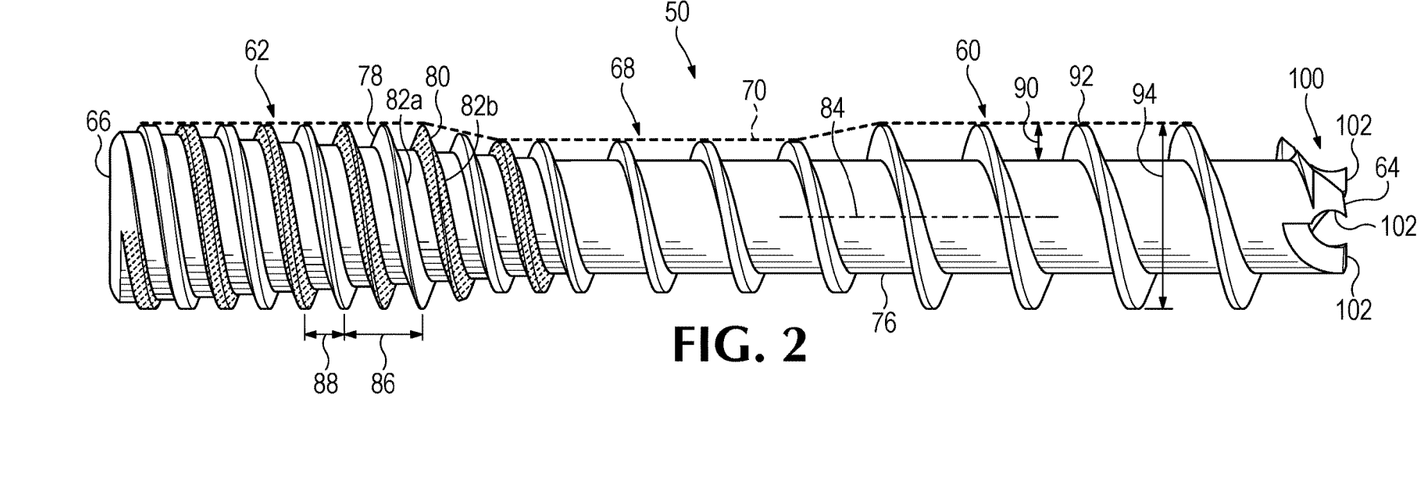
FIG. 2 is a side view of the fastener of FIG. 1, taken as in FIG. 1 but without the bone.
Figure 3:
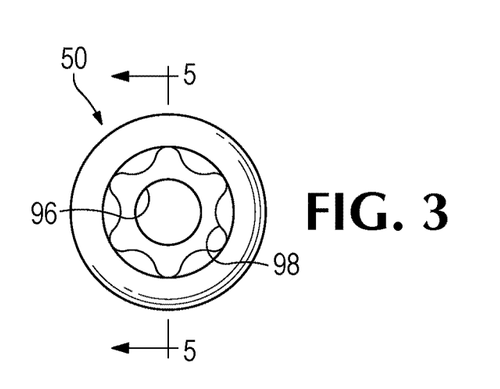
FIG. 3 is a proximal end view of the fastener of FIG. 1.

Fastener 50 has a forward portion 60 (interchangeably called a distal section) and a rear portion 62 (interchangeably called a proximal section) (see FIG. 2). Forward portion 60 extends to a distal end 64 of the fastener. Rear portion 62 extends to a proximal end 66 of the fastener. The forward and rear portions may be considered to be contiguous with one another, or to be separated from one another axially by a midsection of the fastener. For example, the midsection may be a waist portion 68 having a smaller major diameter than the forward and rear portions, as indicated by an imaginary surface of revolution at 70. (Only an upper region of the surface of revolution is shown in FIG. 2.)

Forward portion 60, rear portion 62, and optional waist portion 68 may be placed into any suitable regions of bone when the fastener is installed (see FIGS. 1 and 2). Bone 52 may include softer, more elastic, trabecular bone region 72 (indicated by dots) and harder, denser, cortical bone region 74 (indicated by wavy lines). In some embodiments, forward portion 60 may be installed at least predominantly in trabecular bone region 72, and rear portion 62 may be installed at least predominantly in cortical bone region 74. Accordingly, the forward and rear portions of the fastener may be structured to optimize interaction with these different bone regions, as described further below. Waist portion 68, if present, may be installed in either or both bone regions 72, 74. Discontinuity 54 may be spanned by forward portion 60, rear portion 62, or waist portion 68.

Fastener 50 has a shaft 76, interchangeably called a root portion, body, or core portion, and a plurality of external threads including a first thread 78 and a second thread 80, each projecting from the shaft (see FIG. 2). Second thread 80 is shaded in FIGS. 1 and 2, and in depictions of other fastener embodiments, to facilitate distinguishing the first and second threads from one another.

An external thread is a helical ridge(s) that follows a single helical path. The lead of the thread (and of the path the thread follows) may remain constant or may vary along only part or all of the length of the thread. The lead, when varying, changes smoothly, such as decreasing gradually in a distal to proximal direction. The lead may exhibit no local increase, in a distal to proximal direction, between the ends of the thread. The thread may extend for at least one or a plurality of revolutions 82a (first thread 78) or 82b (second thread 80) about a longitudinal axis 84 of the fastener in portions 60, 62, and/or 68 of the fastener. The thread may be continuous between its opposite ends, or may define one or more gaps at which the thread stops and starts again. Each gap may, for example, correspond to less than two revolutions or less than one revolution of the helical path followed by the thread.

First thread 78 extends from forward portion 60 to rear portion 62 and may be described as a longer thread. The first thread may have a plurality of revolutions in the forward portion, a plurality of revolutions in the rear portion, and at least one or a plurality of revolutions in the waist portion (if present). In some embodiments, the first thread may traverse at least a majority of the length of the forward portion, rear portion, and waist portion (if present). In some embodiments, the first thread may traverse at least about 75%, 80%, 90%, or 95% of the length of the fastener.

Second thread 80 may have a more restricted longitudinal extent than first thread 78, and may be described as a shorter thread that only partially overlaps the first thread longitudinally along the fastener. The second thread may be located at least predominantly or exclusively in rear portion 62, or in rear portion 62 and waist portion 68 of the fastener. In some embodiments, the second thread may traverse at least a majority of the length of the rear portion, such as at least about 75%, 80%, 90% or 95% of the length. Second thread 80 may longitudinally overlap first thread 78 in rear portion 62. In some embodiments, the first thread may extend along at least about 50%, 60%, 70%, 80%, or 90% of the longitudinal extent of the second thread. Accordingly, the first and second threads may have similar longitudinal extents in the rear portion.

The terms "lead" and "pitch" have the following definitions. A lead 86 of a thread (or of a fastener or fastener region) is the axial distance, measured parallel to longitudinal axis 84, spanned by one full revolution of the thread (or of a thread in the fastener or fastener region). In contrast, a pitch 88 of a fastener region is the axial distance, measured parallel to longitudinal axis 84, between adjacent thread revolutions in the fastener region, whether the thread revolutions are provided by the same thread (if the fastener region is single-threaded) or provided by different threads (if the fastener region is multi-threaded). Accordingly, the lead and the pitch of a fastener region are the same when the region is single-threaded but not when the region is double-threaded.

First thread 78 has a lead that decreases in a proximal direction to generate compression when the fastener is driven into bone. The average lead of the first thread may be larger in forward portion 60 than rear portion 62. The average lead also may be larger in the forward portion 60 than waist portion 68, and/or may be larger in the waist portion than rear portion 62. The lead of first thread 78 within one or any combination of the forward, waist, and rear portions may be substantially constant or may decrease toward proximal end 66 of the fastener within the portion. In some embodiments, the lead may vary continuously over a plurality of revolutions within the portion, may remain constant over a plurality of revolutions within the portion, or both. In some embodiments, the lead of first thread 78 decreases within forward portion 60 as the first thread extends toward rear portion 62 and is substantially constant in the rear portion. In some embodiments, such as longer fasteners, the lead of first thread 78 in forward portion 60, from distal to proximal, may be constant for at least one or two revolutions and then may decrease for at least one or two revolutions.

Second thread 80 may match a proximal section of first thread 78. The second thread may extend in parallel with the first thread about longitudinal axis 84, and may have the same lead as first thread 78 in rear portion 62. The first and second threads may be axially offset from one another by less than their lead (e.g., with an axial offset (i.e., the pitch) of about one-half or less of the lead). Accordingly, revolutions of the first and second threads may alternate with one another along rear portion 62 of the fastener. Due to the presence of at least a second thread 80, the pitch of forward portion 60 may be at least about or greater than twice the pitch of rear portion 62.

In some embodiments, rear portion 62 of the fastener further may include a third thread that matches the second thread but is axially offset therefrom by less than one-half of the lead. The rear portion of the fastener thus may be at least triple-threaded.

Each thread may have any suitable height 90 (interchangeably called a depth). The height is the distance, measured radially, between a crest 92 of the thread and shaft 76. Height 90 of first thread 78 may vary between and/or within any portions of the fastener, or may be substantially constant. The maximum height may be present in forward portion 60, to provide effective purchase in trabecular bone (e.g., see FIG. 2). In other embodiments, the average thread height in the forward portion may be the same as or less than the average height in rear portion 62, and may be the same as or less than the average height in waist portion 68 (if present). The height in the waist portion (if present) may be the same as in rear portion 62, or may be less or greater than the height in the rear portion. The height in rear portion 62 may be constant, or may decrease toward proximal end 66 of the fastener (e.g., see FIG. 2), among others. The height of second thread 80 may be similar to the height of first thread 78 in rear portion 62. In exemplary embodiments, the height of the first and second threads in rear portion 62 is less (e.g., at least 25%, 30%, or 40% less) than the height of the first thread in forward portion 60, to provide more effective tapping and purchase in cortical bone.

First thread 78 (and/or the fastener) may have any suitable major diameter 94 (also called an outside diameter). The major diameter may be substantially constant within any portion or combination of fastener portions, or may vary between any portions and/or within any portion. In some embodiments, the major diameter is substantially constant within each portion. The major diameter may (or may not) be the same for the forward and rear portions 60, 62, but smaller therebetween to form waist portion 68. In some embodiments, the major diameter is greater in rear portion 62 than in forward portion 60, and tapers in the rear portion toward the forward portion.

Figure 5:
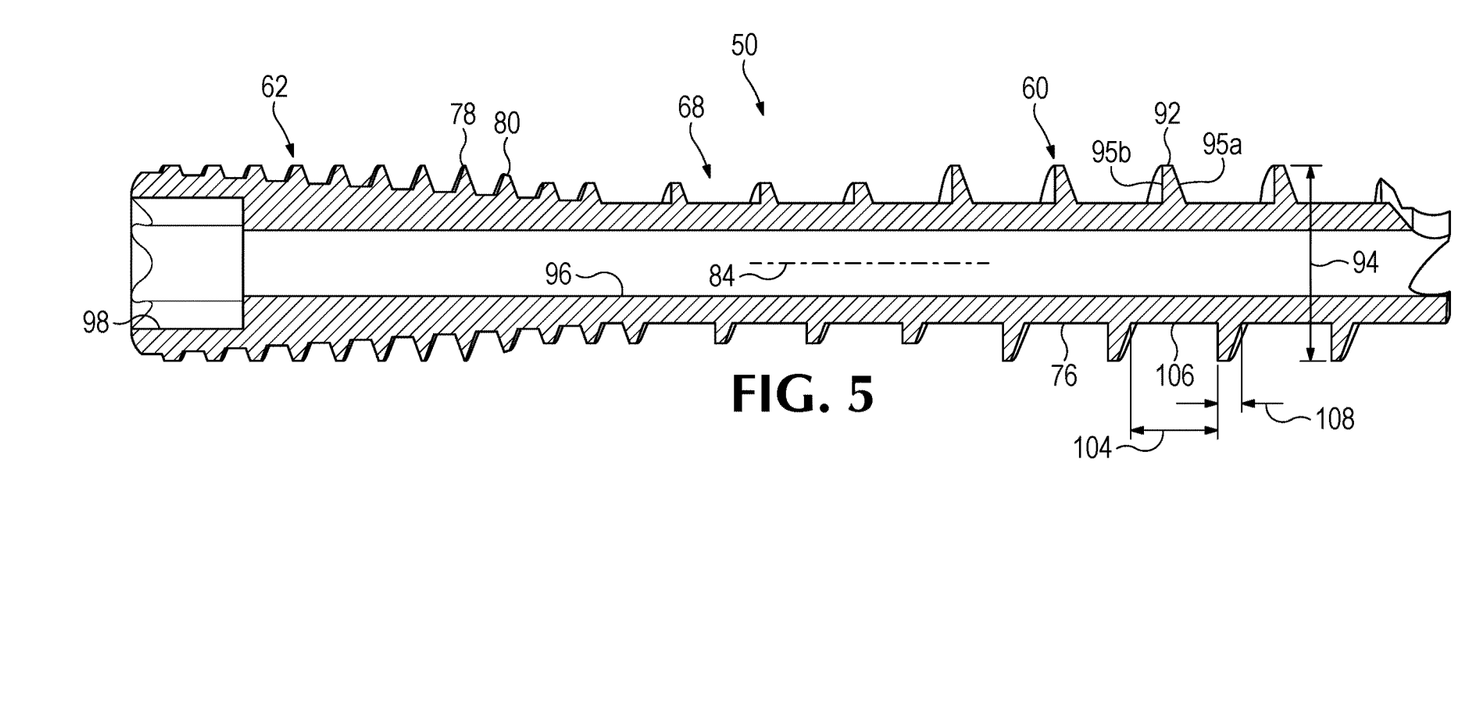
FIG. 5 is a longitudinal sectional view of the fastener of FIG. 1, taken generally along line 5-5 of FIG. 3.

The threadform of first thread 78 may be different in forward portion 60 and rear portion 62 (see FIG. 5). In the forward portion, the first thread may have an asymmetrical, buttress geometry, as shown, in which a distal flank 95*a* is sloped relative to a plane that is orthogonal to longitudinal axis 84, while a proximal flank 95*b* of the thread is orthogonal (or at least relatively more orthogonal) to the plane. In rear portion 62, the first thread (and the second thread) may have a threadform with a more symmetrical geometry (also called a unified geometry), in which proximal and distal flanks 95*a*, 95*b* are sloped to a similar degree, but in opposite directions.

Shaft 76 may have any suitable structure. The shaft may define a channel 96 that extends longitudinally through the fastener (see FIGS. 3-5). The fastener is thus cannulated and can be installed over a guide wire. A proximal end of channel 96 may be enlarged to form a driver-engagement recess 98. The recess has features for rotational coupling with a complementary working end of a driver that turns the fastener about its longitudinal axis for threaded advancement of the fastener into bone.

The shaft, considered conceptually without the threads, may have any suitable diameter, cross-sectional shape, and/or three-dimensional shape in each portion of the fastener. The diameter may correspond to the minor diameter of the fastener or first/second thread thereof. The diameter may be constant within any portion or combination of portions. Alternatively, or in addition, the diameter may taper linearly or nonlinearly toward the distal end of the fastener within any portion or combination of portions. The cross-sectional shape of the shaft may be constant within any portion or combination of portions or may vary within and/or between portions. Cross-sectional shapes that may be suitable include circular or non-circular (e.g., elliptical, polygonal (such as rounded polygonal), wavy, etc.). Suitable three-dimensional shapes for the shaft in each portion or any combination of portions includes cylindrical, conical, or the like. In some embodiments, the shaft is conical or at least tapered in the rear portion and cylindrical in the forward portion. In these embodiments, the shaft in the waist portion (if present) may be cylindrical (e.g., having the same diameter as the shaft in the forward portion), conical (or at least tapered), or a combination thereof. In some embodiments, the shaft is cylindrical in both the forward and rear portions, and has a substantially constant diameter. In some embodiments, the shaft is continuously tapered between the forward and rear portions. In some embodiments, the shaft tapers distally in the rear portion, and has a non-circular cross-sectional shape in the forward portion. In some embodiments, the shaft has a non-circular (e.g., polygonal) cross-sectional shape in both the forward and rear portions, and optionally the same non-circular cross-sectional shape in both portions.

Figure 4:
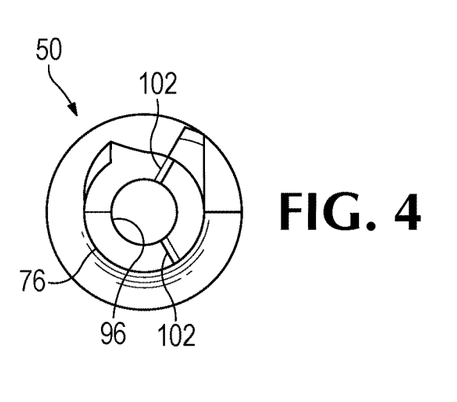
FIG. 4 is a distal end view of the fastener of FIG. 1.

The fastener may be self-drilling and/or self-tapping (see FIGS. 2, 4, and 5). For example, fastener 50 has a self-drilling tip 100, which may include a plurality of end-cutting elements 102. The fastener also or alternatively may have flutes formed in the first thread and/or the second thread, to tap bone by cutting a helical groove therein as the fastener is driven into bone.

The thread configuration of the fastener allows a greater percentage of shaft 76 to be located intermediate revolutions of the first thread in forward portion 60, such that the forward section of the first thread disturbs less trabecular and cortical bone. For example, a width 104 of an exposed area 106 of the shaft, measured axially between adjacent revolutions of the first thread, may be greater than (e.g., at least about 2, 2.5, or 3 times) a width 108 of the first thread measured between distal flank 95a and proximal flank 95b at shaft 76. The lead of the first thread in forward portion 60 may be at least about 2, 2.5, 3, or 3.5 times width 108.

Fastener 50 may have a headless configuration that allows complete insertion into bone. More particularly, the headless configuration may enable the fastener to be advanced into bone until proximal end 66 is substantially flush with or below the surface of the bone, to avoid interference with surrounding tissues (see FIG. 1). Complete insertion may be facilitated by only a gradual increase, if any, in the diameter of the shaft between the distal and proximal ends of the fastener. Also, the maximum diameter of at least one of the threads may be equal to the largest diameter of any part of the fastener. Further aspects of the fasteners of this section are exemplified and described elsewhere herein, such as below in Section IV.

II. COMPOSITION AND MANUFACTURE

This section describes exemplary compositions for, and methods of making, the fasteners of the present disclosure.

The fasteners disclosed herein may have any suitable composition. Each may be formed of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, magnesium or magnesium alloy (e.g., an alloy including magnesium, calcium, and zinc) etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material (i.e., bioresorbable polymer/plastic/metal), such as polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, natural polymers (such as collagen or other polypeptides, polysaccharides (e.g., starch, cellulose, and/or chitosan)), magnesium or magnesium alloy (e.g., an alloy including magnesium, calcium, and zinc); or (4) any combination thereof. In exemplary embodiments, the fastener is formed of metal or bioresorbable or non-resorbable polymer. In exemplary embodiments, the fastener has a single-piece construction (no moving parts), and may be monolithic.

The fastener may be formed by any suitable process or combination of processes. For example, the fastener may be formed by machining, casting, molding, additive manufacturing (also known as 3D printing), and/or the like.

III. METHODS OF FIXING BONE

This section describes exemplary methods of fixing bone using the fasteners of the present disclosure. The method steps of this section may be performed in any suitable order and combination, with a fastener having any combination of features of the present disclosure.

At least one bone to be fixed may be selected. The at least one bone may be a single bone or a pair of bones. The at least one bone may have a discontinuity, such as a fracture, a severing cut, a non-union, an anatomical joint, or the like. Pieces of the bone may be aligned with one another before the fastener is installed, to restore an anatomical shape of the bone.

A guide wire may be placed into the at least one bone, and across the discontinuity. The guide wire may define a trajectory for the fastener. If the guide wire is radiopaque, the trajectory may be visualized by an X-ray-based imaging technique, such as fluoroscopy, to verify that the trajectory is suitable.

A hole for the fastener may be formed in the bone. The hole may be drilled by a separate drill before the fastener is introduced into the bone, such as to a depth that is at least about the length of the fastener. For example, the hole may be drilled over the guide wire using a cannulated drill. Alternatively, the hole may be drilled by the fastener itself using a drilling tip thereof. The hole may have a diameter that corresponds to the outer diameter of the shaft of the fastener and/or that is less than the major diameter of the first thread in the forward portion of the fastener. In some embodiments, if the shaft has a non-circular cross-section, the diameter of the hole may be less than the maximum diameter of the shaft in the forward portion, such as greater than twice the minimum radius of the shaft, and less than twice the maximum radius of the shaft, in a given cross-section of forward portion.

The fastener may be driven into the bone such that the fastener spans the discontinuity in the bone. In some embodiments, the fastener may be inserted into the bone over the guide wire. In some embodiments, the guide wire may be removed after drilling and before driving the fastener into bone.

IV. EXAMPLES

The following examples describe selected aspects and embodiments of the present disclosure related to orthopedic fasteners with single- and multi-threaded regions and methods of using the fasteners to fix bone. The features of the fasteners described in this section may be combined with one another and with any suitable features described above in Sections I-III. These examples are intended for illustration and should not limit the entire scope of the present disclosure.

Example 1. Fastener with No Waist Portion

Figure 6:
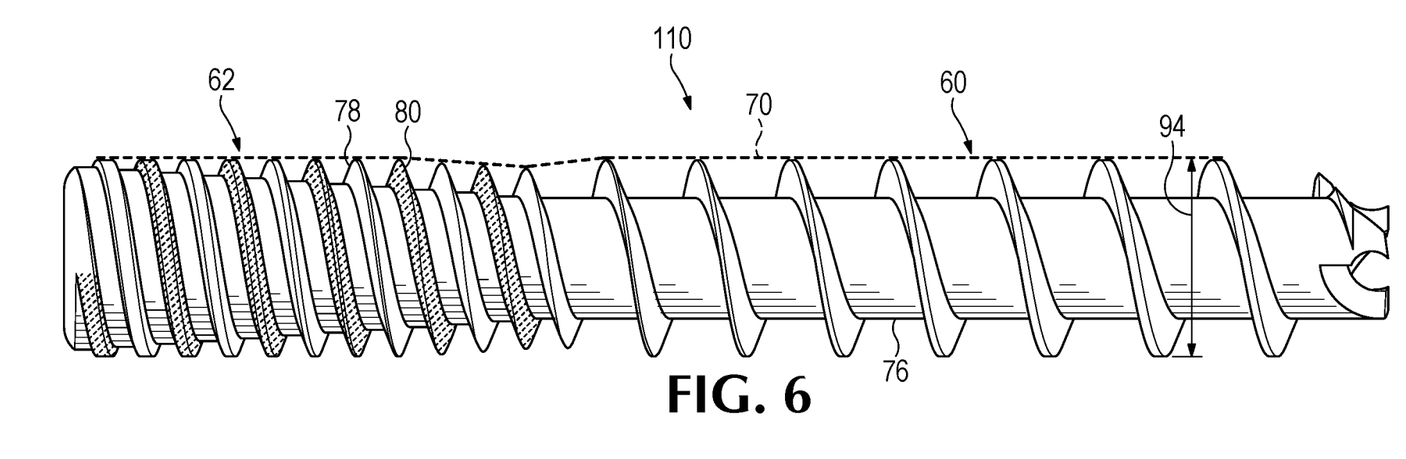
FIG. 6 is a side view of another exemplary fastener that is similar to the fastener of FIG. 1, except having a substantially constant major diameter, in accordance with aspects of the present disclosure.

This example describes an exemplary fastener 110 lacking a substantial waist portion (compare with fastener 50 of FIG. 2); see FIG. 6.

Fastener 110 may have any suitable combination of features described above for fastener 50, including a forward portion 60, a rear portion 62, a shaft 76, and first and second threads 78, 80, among others. However, in contrast to fastener 50, major diameter 94 of fastener may be substantially constant between, and within, forward portion 60 and rear portion 62. Thus, the forward and rear portions may be contiguous with one another, and surface of revolution 70 may be substantially cylindrical.

Example 2. Fastener with Non-Circular Shaft

Figure 7:
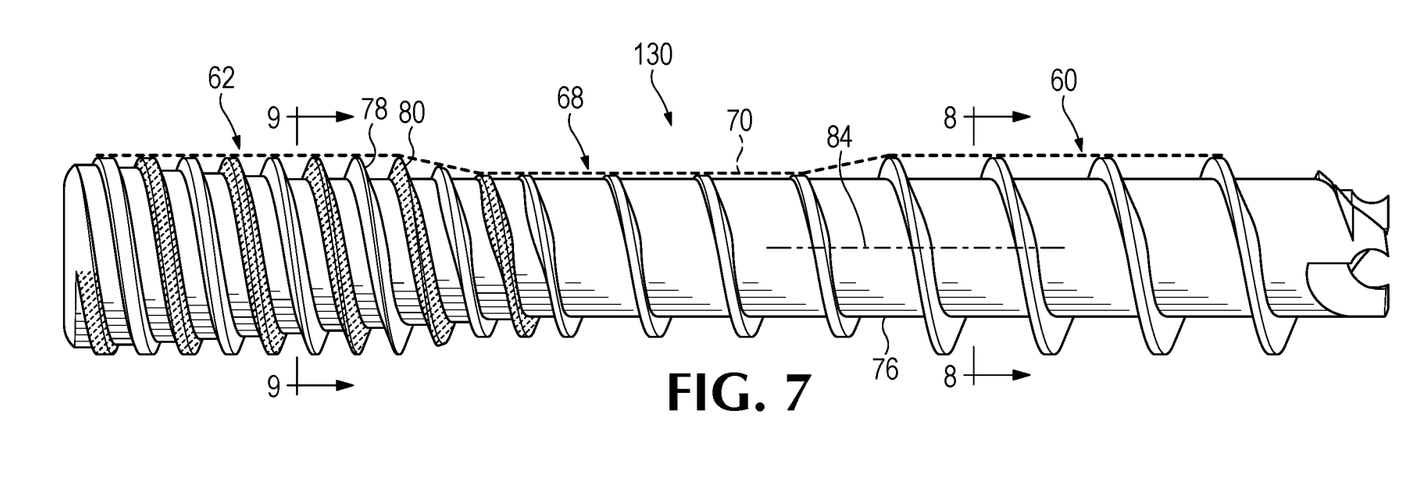
FIG. 7 is a side view of yet another exemplary fastener that is similar to the fastener of FIG. 1, except having a shaft that is triangular in cross-section in the forward portion of the fastener, in accordance with aspects of the present disclosure.
Figure 8:
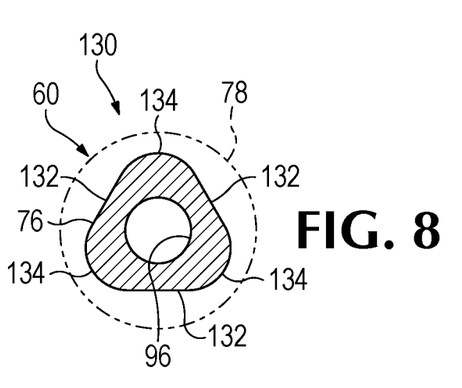
FIG. 8 is a somewhat schematic, cross-sectional view of the fastener of FIG. 7, taken generally along line 8-8 of FIG. 7, and showing the shaft as sectioned, and a first thread in phantom outline as a local orthogonal projection onto the plane of section, to facilitate distinguishing the shaft from the first thread.
Figure 9:
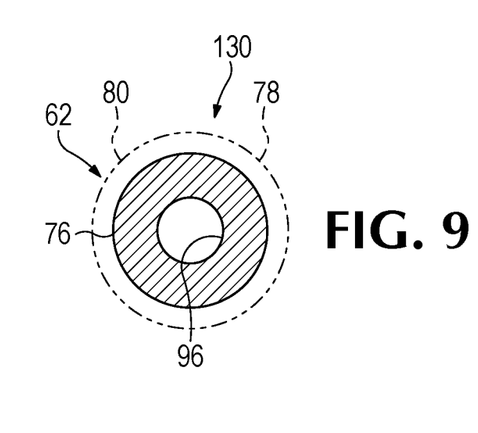
FIG. 9 is another somewhat schematic, cross-sectional view of the fastener of FIG. 7, taken generally along line 9-9 of FIG. 7, and showing the shaft as sectioned, and first and second threads in phantom outline as a local orthogonal projection onto the plane of section, to facilitate distinguishing the shaft from the threads.

This example describes an exemplary fastener 130 having a non-circular shaft 76 in a forward portion of the fastener; see FIGS. 7-9.

Fastener 130 may have any suitable combination of features described above for fastener 50, including a forward portion 60, a rear portion 62, a waist portion 68, a shaft 76, and first and second threads 78, 80, among others. However, in contrast to fastener 50, shaft 76 may have a non-circular cross-sectional shape, taken orthogonally to longitudinal axis 84, in at least part of forward portion 60 (e.g., at least the majority of the length of the forward portion) and/or in at least part of waist portion 68 (e.g., at least the majority of the length of the waist portion). The cross-sectional shape and diameter of the shaft may or may not be substantially constant in and between the forward and waist portions.

Exemplary cross-sectional shapes of shaft 76 for forward and rear portions 60, 62 are shown in FIGS. 8 and 9. In these views, threads 78, 80 are shown in phantom outline as orthogonal projections, parallel to longitudinal axis 84, onto the plane of section, rather than in cross-section, to emphasize the cross-sectional shape of the shaft.

FIG. 8 shows shaft 76 in forward portion 60 having a triangular shape creating three flat (or at least flatter) sides 132 and three lobes 134 (rounded corners). The triangular shape, in combination with an undersized hole in bone (with a diameter less than the diameter of the shaft), may allow the fastener to be driven more easily into bone using a lower insertion torque, and may hold the fastener in place more effectively once inserted. The lobes define the maximum radius of the cross-sectional shape, and urge adjacent bone radially outward as the fastener is rotated. Elasticity of the bone, and/or bone growth during healing, encourages bone to move closer to and/or into contact with flat sides 132, stabilizing the fastener. In other embodiments, the non-circular cross-sectional shape may be polygonal (e.g., with rounded corners), elliptical, wavy, or the like.

FIG. 9 shows shaft 76 in rear portion 62 having a circular cross-sectional shape. The diameter of the shaft in the rear portion may increase gradually toward proximal end of the fastener. In other embodiments, the rear portion also or alternatively may have a non-circular cross-sectional shape as described above, such as the same cross-sectional shape as the forward portion and/or the waist portion of the fastener.

Example 3. Fastener with Tapered Major Diameter

Figure 10:
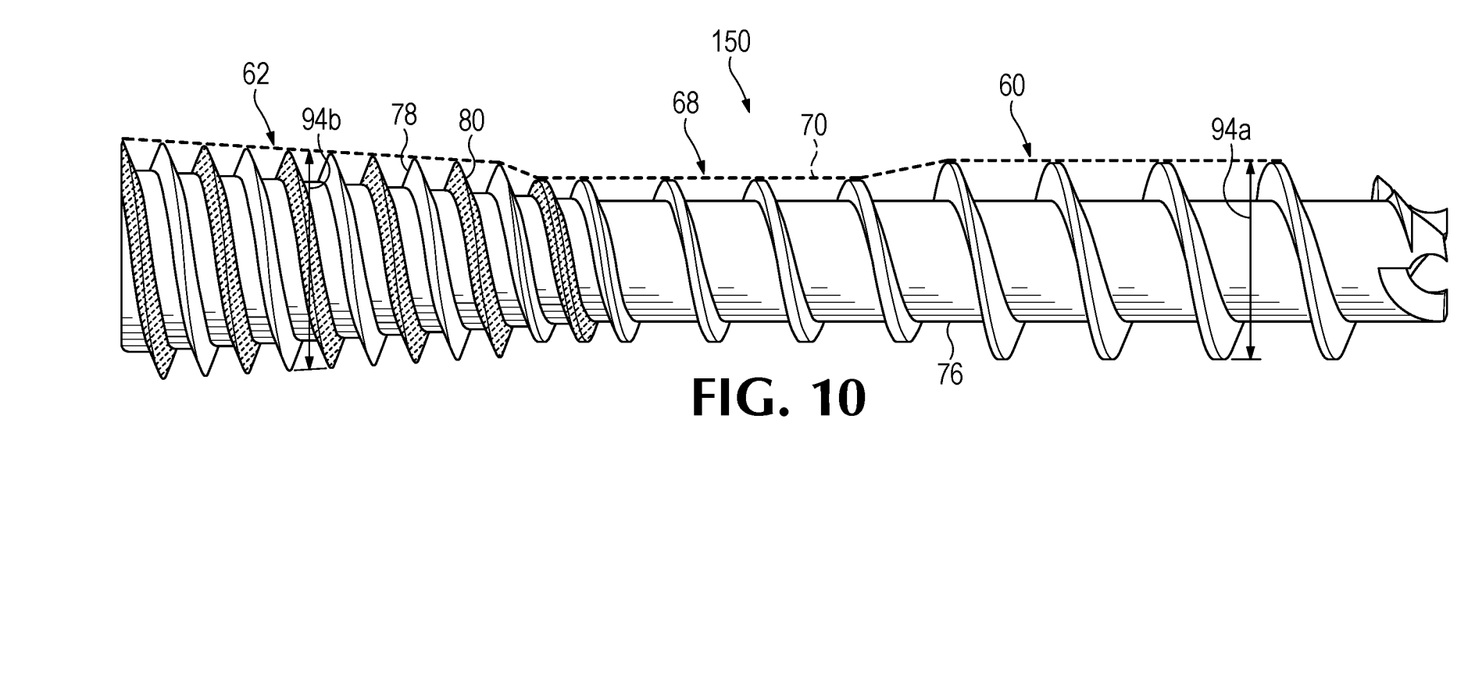
FIG. 10 is a side view of still another exemplary fastener that is similar to the fastener of FIG. 1, except having a constant thread height in the rear portion of the fastener, in accordance with aspects of the present disclosure.

This example describes an exemplary fastener 150 having a tapered major diameter in a rear portion 62 of the fastener; see FIG. 10.

Fastener 150 may have any suitable combination of features described above for fastener 50, including a forward portion 60, a rear portion 62, a waist portion 68, a shaft 76, and first and second threads 78, 80, among others. However, in contrast to fastener 50, the height of threads 78, 80 in rear portion 62 is constant. The constant height, combined with a tapered shaft in the rear portion, results in a tapered major diameter. In the depicted embodiment, major diameter 94a of the fastener in forward portion 60 is less than major diameter 94b in rear portion 62. More particularly, threads 78, 80 in the rear portion have major diameter 94b that tapers to substantially the same value as major diameter 94a. In other embodiments, major diameter 94b may taper to a value that is greater or less than the value of major diameter 94a.

Example 4. Selected Embodiments

This example describes selected embodiments of the present disclosure as a series of numbered paragraphs.

Paragraph 1. A fastener for fixing bone, comprising: (A) a forward portion; (B) a rear portion; (C) a first thread having a plurality of revolutions in each of the forward and rear portions; and (D) a second thread having a plurality of revolutions in the rear portion; wherein the first thread has a greater average lead in the forward portion than the rear portion, wherein revolutions of the first thread and the second thread alternate with one another in the rear portion, wherein, optionally, the forward portion is a substantially single-threaded forward portion, wherein, optionally, the rear portion is an at least double-threaded rear portion, and wherein, optionally, the second thread has no revolutions in the front portion.

Paragraph 2. The fastener of paragraph 1, wherein the first thread has a greater average height in the forward portion than the rear portion.

Paragraph 3. The fastener of paragraph 1 or paragraph 2, wherein the first thread extends continuously from the forward portion to the rear portion.

Paragraph 4. The fastener of any one of paragraphs 1 to 3, wherein the first and second threads project from a shaft, wherein the first thread has a width measured at the shaft, and wherein the average lead of the first thread in the forward portion is at least about three times the average width of the first thread in the forward portion.

Paragraph 5. The fastener of any one of paragraphs 1 to 4, wherein the fastener includes a waist portion located intermediate the forward portion and the rear portion, wherein the first thread has at least one revolution in the waist portion, and wherein the average major diameter of the at least one thread revolution in the waist portion is less than the average major diameter of the plurality of revolutions of the first thread in the forward portion and less than the average major diameter of the plurality of revolutions of the first thread in the rear portion.

Paragraph 6. The fastener of paragraph 5, wherein the first thread has an average lead in each portion, wherein the average lead is larger in the forward portion than the waist portion, and larger in the waist portion than the rear portion.

Paragraph 7. The fastener of any one of paragraphs 1 to 6, wherein the fastener has a shaft from which the first thread and the second thread project.

Paragraph 8. The fastener of paragraph 7, wherein the shaft in the rear portion is tapered toward the forward portion.

Paragraph 9. The fastener of paragraph 8, wherein the shaft is cylindrical in the forward portion.

Paragraph 10. The fastener of paragraph 7, wherein the shaft has a non-circular cross-sectional shape in a plane orthogonal to a longitudinal axis of the fastener in at least one portion.

Paragraph 11. The fastener of paragraph 10, wherein the cross-sectional shape is polygonal.

Paragraph 12. The fastener of any one of paragraphs 7, 8, 10, and 11, wherein the shaft has a plurality of distinct, non-cylindrical sides in the at least one portion, and wherein the non-cylindrical sides are arranged about a longitudinal axis of the fastener from one another.

Paragraph 13. The fastener of paragraph 12, wherein each of the non-cylindrical sides is spaced from the longitudinal axis by a distance, and wherein each of the noncylindrical sides is flattened relative to a cylinder having the distance as its radius.

Paragraph 14. The fastener of any one of paragraphs 1 to 13, wherein the lead of the first thread in the forward portion decreases gradually toward the rear portion.

Paragraph 15. The fastener of any one of paragraphs 1 to 14, wherein the lead of the first thread varies in the forward portion and is constant in the rear portion.

Paragraph 16. The fastener of any one of paragraphs 1 to 15, wherein the first thread has a buttress threadform in the forward portion and a symmetrical threadform in the rear portion.

Paragraph 17. The fastener of any one of paragraphs 1 to 16, wherein the forward portion has a pitch that is more than twice a pitch of the rear portion.

Paragraph 18. The fastener of any one of paragraphs 1 to 17, wherein the fastener is cannulated.

Paragraph 19. The fastener of any one of paragraphs 1 to 18, wherein the maximum major diameter of one of the threads is the largest diameter of the fastener.

Paragraph 20. The fastener of any one of paragraphs 1 to 19, wherein the fastener further comprises a cutting tip configured to make the fastener self-drilling, and/or wherein the fastener is self-tapping.

Paragraph 21. A method of fixing bone, the method comprising: (A) selecting the fastener of any one of paragraphs 1 to 20; and (B) driving the fastener into at least one bone such that the fastener spans a discontinuity formed by the at least one bone.

Paragraph 22. The method of paragraph 21, further comprising a step of placing a guide wire in the at least one bone, to facilitate the step of driving the fastener into the at least one bone.

Paragraph 23. The method of paragraph 21 or paragraph 22, wherein the step of driving places the fastener into (a) a single bone and across at least one discontinuity defined by the single bone, with the discontinuity selected from the group consisting of a fracture, a cut, and a nonunion, or (b) into a pair of bones and across a discontinuity formed between the pair of bones.

Paragraph 24. The method of any one of paragraphs 20 to 23, wherein the step of driving the fastener includes a step of seating the fastener so that its proximal end is substantially flush with or below a surface of the at least one bone to avoid interference with surrounding tissues.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of fixing bone, the method comprising:
selecting a fastener including a forward portion, a rear portion, a first thread having a plurality of revolutions in each of the forward and rear portions, and a second thread having a plurality of revolutions in the rear portion and none in the forward portion, wherein the first thread has a greater average lead in the forward portion than the rear portion, and wherein revolutions of the first thread and the second thread alternate with one another in the rear portion such that the rear portion is at least double-threaded; and
driving the fastener into at least one bone such that the fastener spans a discontinuity formed by the at least one bone.

2. The method of claim 1, wherein the first thread has a greater average height in the forward portion than the rear portion.

3. The method of claim 1, wherein the first thread extends continuously from the forward portion to the rear portion.

4. The method of claim 1, wherein the first and second threads project from a shaft, wherein the first thread has a width measured at the shaft, and wherein the average lead of the first thread in the forward portion is at least about three times an average width of the first thread in the forward portion.

5. The method of claim 1, wherein the fastener includes a waist portion located intermediate the forward portion and the rear portion, wherein the first thread has at least one revolution in the waist portion, and wherein an average major diameter of the at least one thread revolution in the waist portion is less than an average major diameter of the plurality of revolutions of the first thread in the forward portion and less than an average major diameter of the plurality of revolutions of the first thread in the rear portion.

6. The method of claim 5, wherein the first thread has an average lead in each portion, wherein the average lead is larger in the forward portion than the waist portion, and larger in the waist portion than the rear portion.

7. The method of claim 1, wherein the fastener has a shaft from which the first thread and the second thread project, and wherein the shaft in the rear portion is tapered toward the forward portion.

8. The method of claim 1, wherein the fastener has a shaft from which the first thread and the second thread project, and wherein the shaft has a non-circular cross-sectional shape in a plane orthogonal to a longitudinal axis of the fastener, along at least a portion of the shaft.

9. The method of claim 8, wherein the cross-sectional shape is polygonal.

10. The method of claim 1, wherein the fastener has a shaft from which the first thread and the second thread project, and wherein the at least a portion of the shaft has a plurality of distinct, non-cylindrical sides, and wherein the non-cylindrical sides are arranged about a longitudinal axis of the fastener from one another.

11. The method of claim 10, wherein each of the non-cylindrical sides is spaced from the longitudinal axis by a distance, and wherein each of the non-cylindrical sides is flattened relative to a cylinder having the distance as its radius.

12. The method of claim 1, wherein the lead of the first thread in the forward portion decreases gradually toward the rear portion.

13. The method of claim 1, wherein the lead of the first thread varies in the forward portion and is constant in the rear portion.

14. The method of claim 1, wherein the first thread has a buttress threadform in the forward portion and a symmetrical threadform in the rear portion.

15. The method of claim 1, wherein the forward portion has a pitch that is more than twice a pitch of the rear portion.

16. The method of claim 1, wherein the step of driving places the fastener into (a) a single bone and across at least one discontinuity defined by the single bone, with the discontinuity selected from the group consisting of a fracture, a cut, and a nonunion, or (b) into a pair of bones and across a discontinuity formed between the pair of bones.

17. The method of claim 1, wherein the step of driving the fastener includes a step of seating the fastener so that its proximal end is substantially flush with or below a surface of the at least one bone to avoid interference with surrounding tissues.

18. The method of claim 1, wherein the maximum major diameter of one of the threads is the largest diameter of the fastener.

19. The method of claim 1, wherein the fastener further comprises a cutting tip configured to make the fastener self-drilling, and/or wherein the fastener is self-tapping.

20. A method of fixing bone, the method comprising:
selecting a fastener including a substantially single-threaded forward portion, an at least double-threaded rear portion, a first thread having a plurality of revolutions in each of the forward and rear portions, and a second thread having a plurality of revolutions in the rear portion, wherein the first thread has a greater average lead in the forward portion than the rear portion, and wherein revolutions of the first thread and the second thread alternate with one another in the rear portion; and
driving the fastener into at least one bone such that the fastener spans a discontinuity formed by the at least one bone.

* * * * *